United States Patent
Kawasaki et al.

(10) Patent No.: US 6,468,950 B1
(45) Date of Patent: Oct. 22, 2002

(54) DENTURE DETERGENTS CONTAINING ANTIMICROBIAL METAL IONS

(75) Inventors: Koji Kawasaki, Kishiwada (JP); Masahiro Kubo, Higashiosaka (JP); Takeo Fujitani, Tondabayashi (JP)

(73) Assignees: Kyowa Limited, Osaka (JP); Shionogi & Co., Ltd., Osaka (JP)

( * ) Notice: Subject to any disclaimer, the term of this patent is extended or adjusted under 35 U.S.C. 154(b) by 0 days.

(21) Appl. No.: 09/673,792
(22) PCT Filed: Apr. 19, 1999
(86) PCT No.: PCT/JP99/02055
  § 371 (c)(1),
  (2), (4) Date: Oct. 20, 2000
(87) PCT Pub. No.: WO99/56714
  PCT Pub. Date: Nov. 11, 1999

(30) Foreign Application Priority Data

Apr. 30, 1998 (JP) .......................................... 10-120454

(51) Int. Cl.$^7$ ................................................ C11D 3/48
(52) U.S. Cl. ................ 510/116; 510/117; 510/125; 510/382; 510/445; 510/446; 510/508; 510/509; 510/510; 510/511; 510/512
(58) Field of Search ................................ 510/116, 117, 510/125, 382, 445, 446, 508, 509, 510, 511, 512

(56) References Cited

U.S. PATENT DOCUMENTS

| | | | | |
|---|---|---|---|---|
| 4,082,841 A | * | 4/1978 | Pader | 424/50 |
| 5,009,898 A | | 4/1991 | Sakuma et al. | 424/618 |
| 5,151,122 A | | 9/1992 | Atsumi et al. | 106/35 |
| 5,268,174 A | | 12/1993 | Sakuma et al. | 424/193.1 |
| 5,468,489 A | * | 11/1995 | Sakuma et al. | 424/49 |
| 5,688,492 A | * | 11/1997 | Galley et al. | 424/49 |
| 5,827,505 A | * | 10/1998 | Hughes et al. | 424/49 |

FOREIGN PATENT DOCUMENTS

| | | | |
|---|---|---|---|
| JP | 3-002113 | * | 1/1991 |
| JP | 4-316511 | | 11/1992 |
| JP | 5-117135 | | 5/1993 |
| JP | 9-175968 | | 7/1997 |
| JP | 9-323936 | | 12/1997 |
| JP | 9323936 | * | 12/1997 |
| JP | 11-49625 | | 2/1999 |

* cited by examiner

Primary Examiner—Charles Boyer
(74) Attorney, Agent, or Firm—Wenderoth, Lind & Ponack, LLP

(57) ABSTRACT

The present invention provides a novel microbicide for a detergent comprising an inorganic carrier conjugated with an antimicrobial metal ion, and a denture detergent containing said microbicide.

9 Claims, 3 Drawing Sheets

Candida albicans A

- ● Apacider AK      $\log_{10} N_t = -0.018 t + 4.297$
- ▲ Silverace A-903K  $\log_{10} N_t = -0.006 t + 5.126$
- ■ Rasap AN-600SA    $\log_{10} N_t = -0.027 t + 4.390$
- ⊞ Novaron AGZ330    $\log_{10} N_t = -0.006 t + 5.238$
- ◆ Zeomic AW10D      $\log_{10} N_t = -0.072 t + 3.926$
- ⊕ Amenitop Ver-III  $\log_{10} N_t = -0.001 t + 5.159$
- ◇ Control           $\log_{10} N_t = -0.001 t + 5.117$ Streptcoccus pneumiae ATCC 49619

| | | |
|---|---|---|
| ● | Apacider AK | $\log_{10} N_t = -1.780\, t + 5.340$ |
| ▲ | Silverace A-903K | $\log_{10} N_t =$   〃 |
| ■ | Rasap AN-600SA | $\log_{10} N_t =$   〃 |
| ⊞ | Novaron AGZ330 | $\log_{10} N_t =$   〃 |
| ◆ | Zeomic AW10D | $\log_{10} N_t =$   〃 |
| ⊕ | Amenitop Ver-III | $\log_{10} N_t =$   〃 |
| ✧ | Control | $\log_{10} N_t = -0.004\, t + 5.050$ |

Staphylococcus aureus IFO 3060

| | | |
|---|---|---|
| ● | Apacider AK | $\log_{10} N_t = -0.047\,t + 4.860$ |
| ▲ | Silverace A-903K | $\log_{10} N_t = -0.084\,t + 4.875$ |
| ■ | Rasap AN-600SA | $\log_{10} N_t = -0.090\,t + 5.196$ |
| ⊞ | Novaron AGZ330 | $\log_{10} N_t = -0.045\,t + 5.340$ |
| ◆ | Zeomic AW10D | $\log_{10} N_t = -0.164\,t + 4.772$ |
| ⊕ | Amenitop Ver-III | $\log_{10} N_t = -0.015\,t + 5.365$ |
| ✤ | Control | $\log_{10} N_t = -0.001\,t + 5.669$ |

DENTURE DETERGENTS CONTAINING ANTIMICROBIAL METAL IONS

TECHNICAL FIELD

The present invention relates to a microbicide for detergents and to a denture detergent comprising the microbicide.

BACKGROUND ART

It is important to prevent microbial contamination by a detergent having microbicidal effect for keeping sanitary life environment, and therefore, microbicides useful for detergents are greatly necessitated. Such microbicides have been presently used in various detergents.

Microbicide is generally required to satisfy the conditions that it exhibits microbicidal effect extensively on various microorganisms in nature, that it is effective in a small amount, and that it is non-toxic, non-stimulative and safe to a living body. In the case that the microbicide is used in combination with a detergent, such as a microbicide for detergents, it would be further required that it is stable in a detergent formulation, that its microbicidal effect is not inhibited by pH and other ingredients, and that it does not spoil the function, color and flavor of the detergent, in addition to the requirements above described.

Microbicides are often used in a denture detergent, which is a sort of detergents, like in other detergents. Since it is difficult to completely remove the indigenous microbiota in mouth only by the action of the detergent, these indigenous microbiota are usually sterilized by the action of a microbicide contained in a denture detergent. One of the serious problems for users of dentures is "peculiar halitosis", and such halitosis is caused by proliferation of the indigenous microbiota in mouth. One of the indigenous microbiota in mouth, *Candida albicans,* is also a pathogen of denture stomatitis. Thus, in view of prevention of the halitosis and denture stomatitis, it is greatly important to use a microbicide in a denture detergent. Microbicides contained in commercially available denture detergents are active oxygen generating agents, such as peroxides, or enzymes, and denture cleaning is conducted by using one of them alone or in combination of two or more of them.

Although it has been studied for finding a microbicide that can exhibit higher microbicidal effect within shorter time compared to the above-mentioned conventional microbicides for denture detergents, practically usable microbicide has not yet been found. The main reason of said less usable microbicide is due to the inhibition of the microbicidal effect of the microbicide by the interaction with other ingredient(s) in a detergent. For example, in the case that sodium lauryl sulfate, which is preferably and widely used as a detergent ingredient in mouthwashes and denture detergents, is used as a detergent ingredient together with a cationic microbicide such as cetylpyridinium chloride and dequalinium chloride, they react with each other to form a white insoluble material, which results in inhibition of the microbicidal effect. In the case that sodium lauryl sulfate is used as a detergent ingredient together with a microbicidal ingredient such as sodium salicylate, phenyl salicylate, and the like, they would not cause inhibition of the microbicidal effect. However, when this combination is used in a denture cleaning, it will provide rather unpleasant feeling than refreshing feeling in the mouth of the denture user after the denture cleaning.

When a nonionic surfactant, such as Amisol MDE, Amisol LME, Emulgen 950 and Emulgen PP-290, is used as a detergent ingredient in combination with a microbicide such as cetylpyridinium chloride, which is inert to the surfactant, the detergent cannot exhibit sufficient detergent and effervescent effects contrary to a detergent containing sodium lauryl sulfate, and hence, it cannot achieve to desired detergent function.

DISCLOSURE OF THE INVENTION

It is an object of the present invention to provide a microbicide for detergents exhibiting excellent microbicidal effect within shorter time in comparison with conventional microbicides for detergents, without inhibition of the microbicidal effects by other ingredient in the detergent, and a denture detergent comprising said microbicide. It is another object of the present invention to provide a microbicide for detergents, which does not inhibit the action of a detergent comprising sodium lauryl sulfate having superior detergent and effervescent effects. It is yet another object of the present invention to provide a denture detergent, which has a superior microbicidal effect with keeping the excellent detergent and effervescent actions of sodium lauryl sulfate, and is comfortably used.

The present inventors have extensively studied to achieve the objects described above and found that an inorganic carrier conjugated with an antimicrobial metal ion, which may be hereinafter referred to as "the microbicide of the invention", is extremely superior as a microbicide for detergents. Thus, the microbicide of the invention has superior microbicidal effect, and it exhibits the superior microbicidal effect within a short time since the microbicidal effect is not inhibited by other ingredients in the detergent.

Thus, the present invention provides a microbicide for detergents comprising an inorganic carrier conjugated with an antimicrobial metal ion. Furthermore, the present invention provides a denture detergent comprising an inorganic carrier conjugated with an antimicrobial metal ion.

Inorganic carriers conjugated with an antimicrobial metal ion have been hitherto mixed with materials such as synthetic resins, rubber materials, paints, synthetic fiber and papers for the purpose of enhancing the antimicrobial property of these materials. Such antimicrobial materials have been used in various fields, such as electric home appliances, house furnishings, office supplies, building materials, wrappings, medical supplies, and the like. However, the present inventors have first found that such inorganic carriers conjugated with an antimicrobial metal ion are effective for improving the microbicidal property of a detergent and exhibit their microbicidal effect on a subject to be cleaned.

BEST MODE FOR CARRYING OUT THE INVENTION

Figure 1:
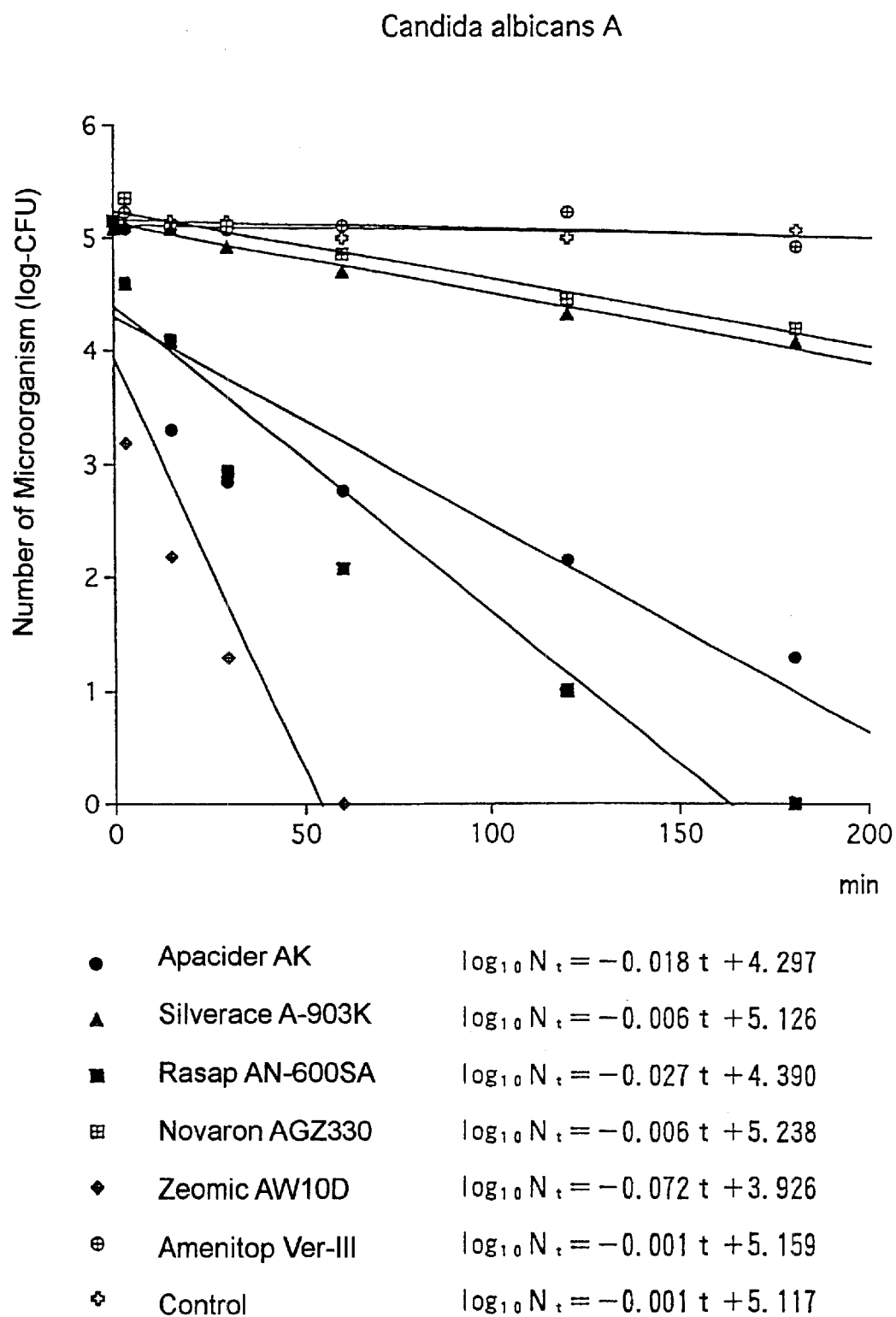
FIG. 1 is a graph showing the microbicidal effect of each microbicide on Candida.

The first embodiment of the invention is a microbicide for detergents comprising an inorganic carrier conjugated with an antimicrobial metal ion.

Although the microbicide for detergents of the invention can be used for any detergent, preferred detergent intended by the present invention is a denture detergent.

The antimicrobial metal ion to be used for conjugation with an inorganic carrier includes silver, copper, and zinc ion. Preferred antimicrobial metal ion is silver ion. The inorganic carrier to be used for conjugating with an antimicrobial metal ion of the invention includes, for example, calcium phosphate, calcium silicate, calcium carbonate, aluminum phosphate, zirconium phosphate, zeolite, silica gel, etc. Preferred inorganic carrier of the invention is calcium phosphate, aluminum phosphate, zirconium phosphate or zeolite. More preferred inorganic carrier is hydroxyapatite, calcium phosphate, or calcium hydrogen phosphate. Further preferred inorganic carrier is hydroxyapatite, or tricalcium phosphate. Most preferred inorganic carrier is hydroxyapatite.

The inorganic carrier conjugated with an antimicrobial metal ion can be prepared according to the methods as described in literatures. For example, when the inorganic carrier is calcium phosphate, silicate or carbonate, it can be prepared by substantially the same method as described. in Japanese Patent Publication No. 218765/1991, which is herein incorporated by reference. Briefly, it is prepared by adsorbing a salt of an antimicrobial metal on a pulverized inorganic carrier, and calcining the resultant at a temperature that the inorganic carrier shrinks so that the metal is not desorbed from the inorganic carrier into water.

When the inorganic carrier is tricalcium phosphate, it can be prepared according to the method as described in Japanese Patent Publication No. 84870/1997, which is herein incorporated by reference. Briefly, it can be prepared conjugating an antimicrobial metal ion on tricalcium phosphate by means of adsorption or ion exchange, or alternatively by producing tricalcium phosphate from an aqueous solution of a soluble calcium salt (e.g., calcium chloride) and disodium hydrogen phosphate or ammonium hydrogen phosphate under an ammonia alkaline condition in the presence of an antibacterial metal salt.

The inorganic carrier conjugated with an antimicrobial metal ion is commercially available in various forms. Commercially available inorganic carriers conjugated with an antimicrobial metal ion include, for example, Silverace A-903K (trade name of calcium phosphate manufactured by Taihei Chemical Industrial Co., Ltd.), Novaron AGZ330 (trade name of zirconium phosphate manufactured by Toagosei Co., Ltd.), Rasap AN-600SA (trade name of aluminum phosphate manufactured by Rasa Industries, Ltd.), Apacider AK (trade name of hydroxyapatite manufactured by Sangi Co., Ltd.), Zeomic AW10D (trade name of zeolite manufactured by Shinanen Co., Ltd.), Amenitop VerIII (trade name of complex compound silver thiosulfato.silica gel manufactured by Matsushita Electric Industrial Co., Ltd.), etc.

The inorganic carrier conjugated with an antimicrobial metal ion of the invention is most preferably Apacider. Apacider is a hydroxyapatite conjugated with silver ion, and several grades of products different in specifications and particle diameters, etc. are commercially available, such as Apacider AW (general grade, calcined form); Apacider A25 (special grade, calcined form); Apacider NB (special grade, non-calcined form); Apacider AK (microparticle grade, calcined form). Most preferred microbicide for detergents of the invention is a commercially available product in the name of Apacider AK (Sangi Co., Ltd.; microparticle grade, calcined form, average particle diameter: 0.3 μm).

The second embodiment of the invention is a denture detergent comprising the micorobicide for detergent of the invention. The denture detergent of the invention contains the microbicide for detergents in an amount of 0.05–10% by weight, preferably 0.1–3% by weight based on the weight of the denture detergent. If the amount is less than the above range, it has less microbicidal activity and cannot achieve the intended object. On the other hand, when the microbicide is contained in an amount larger than the above range, it is not preferable to use in formulating into a tablet, because the resultant tablet would decrease in its hardness to cause capping during a tabletting process, and further abrasion or clacking during a distribution of the product.

The denture detergent of the invention can be formulated into various forms such as effervescent tablets, effervescent granules, effervescent powders, liquids, and teeth pastes. Preferred formulation is an effervescent tablet.

The denture detergent of the invention may further contain a detergent ingredient, a bleaching ingredient, an effervescent ingredient, and an active oxygen generating material, etc., in addition to the microbicide of the invention. The term "coated", as used herein for the ingredients contained in the denture detergent of the invention, means that the ingredient is coated with an appropriate coating agent to avoid interaction with other ingredients coexisting in the formulation. For example, the terms "coated sodium percarbonate" and "coated citric acid" refer to sodium percarbonate and citric acid coated with an adequate coating agent, respectively. The coating method may be any conventional coating methods. For instance, coating may be conducted simultaneously with a granulation step by means of spray granulation, rolling granulation or the like, or after the granulation step by pan coating, flow coating, dry coating or the like. The detergent ingredients include alkyl sulfate salts such as sodium lauryl sulfate, triethanolamine lauryl sulfate, sodium cetyl sulfate, sodium lauroyl sarcosinate, sodium di-2-ethylhexylsulfosuccinate, sodium lauryl phosphate, alkylbenzenesulfonate, α-olefin sulfonate and the like. Especially, sodium lauryl sulfate is preferable, since it has superior detergent effect on tobacco tar, etc., and its detergent effect can be visually and psychologically realized from effervescence, and it does not provide unpleasant feeling in mouth after using. The microbicide for detergent of the invention does not give undesired decrease of microbicidal effect due to interactions among ingredients, contrary to the case of combination of cetylpyridium chloride and sodium lauryl sulfate, since the microbicide for detergents of the invention does not react with sodium lauryl sulfate. The combination of the microbicide of the invention and sodium lauryl sulfate is very preferable in that the microbicide ingredient and the detergent ingredient can satisfactorily exhibit their superior microbicidal, detergent and effervescent effects, respectively. The detergent ingredient is usually used in an amount of 1–30% by weight, preferably 1–20% by weight. In case of sodium lauryl sulfate, it is used in an amount of 1–15% by weight, preferably 3–10% by weight.

For the bleaching ingredients, the combination of a peroxide such as sodium perborate, sodium percarbonate, or the like, and sodium peroxysulfate or potassium hydrogen monopersulfate (e.g., OXONE; manufactured by Du Pont) can be used as an active oxygen generating agent. Alternatively, a chlorine microbicide (e.g., sodium hypochlorite, sodium dichloroisocyanuate, sodium trichloroisocyanurate, etc.), sodium percarbonate or OXONE may be used. Optionally, the bleaching ingredients may be coated with a coating agent. A preferred coating agent is a mixture of a magnesium, alkali metal or calcium salt of an aromatic hydrocarbon sulfonic acid, a sulfate ester of an alkyl aromatic hydroxy hydrocarbon ethylene oxide adduct, higher fatty acid alcohol sulfate ester or a sulfate ester of a higher fatty acid alcohol ethylene oxide adduct, and an alkali silicate, carbonate, bicarbonate or sulfate. A preferred bleaching ingredient is a combination of a coated sodium percarbonate and OXONE. The coated sodium percarbonate preferably coated by a mixture of an alkali metal salt of an aromatic hydrocarbon sulfonic acid and an alkali silicate salt. The bleaching agent is used in an amount of 20–70% by weight, preferably 30–60% by weight. When the combination of a coated sodium percarbonate and OXONE is used, the amount of the former is in the range of 15–45%, preferably 25–40% by weight, and the amount of the latter is in the range of 5–20%, preferably 5–15% by weight.

For the effervescent ingredient, a combination of a carbonate or bicarbonate such as sodium hydrogen carbonate, sodium carbonate, potassium hydrogen carbonate, and an organic acid such as citric acid, succinic acid, sulfamic acid or an inorganic acid is used. Optionally, the acid may be coated with a coating agent. A preferred coating agent is acetyl cellulose, gum arabic, sodium alginate, soluble starch, hydroxy propyl cellulose, wheat starch, food polysaccharides such as sucrose, lactose and the like. A preferred effervescent ingredient is a combination of a coated citric acid and sodium hydrogen carbonate. A food saccharide is especially preferable as a coating agent of the coated citric acid. The amount of the effervescent ingredient is in the range of 5–30% by weight for a carbonate or bicarbonate and in the range of 5–45% by weight for an organic or inorganic acid. Preferably, a carbonate or bicarbonate is used in an amount of 8–25% by weight, and an organic or inorganic acid is used in an amount of 10–40% by weight. When a coated citric acid and sodium hydrogen carbonate are used, the amount of the former is in the range of 10–40% by weight, preferably 15–35% by weight, and the amount of the latter is in the range of 5–25%, preferably 8–20% by weight.

In addition to the above ingredients, the denture detergent of the invention may contain a lubricant such as silicon dioxide, synthetic aluminum silicate, magnesium carbonate, magnesium stearate, talc, calcium stearate, hydrogenated castor oil or magnesium hydroxide in an amount of 0.1–3% by weight, preferably 0.3–2% by weight. Preferably, synthetic aluminum silicate is added in an amount of 0.1–3% by weight, more preferably 0.3–1.5% by weight.

Also, the denture detergent of the invention may further contain a stabilizing agent such as sodium sulfite, sodium edetate, magnesium chloride, calcium citrate, magnesium oxide or sodium thiosulfate in an amount of 0.5–15% by weight, preferably 1–10% by weight. Preferably, magnesium oxide is added in an amount of 1–5% by weight, more preferably 1.5–3% by weight.

Further, a humectant (e.g., propylene glycol, polyethylene glycol, sorbitol, glycerol, glycerol monostearate, polysorbate 80, liquid petrolatum), a solubilizing agent (e.g., hydrogenated castor oil, vestibule oils, polyoxyethylene nonylphenyl ether, sugar ester), a flavor (e.g., saccharin sodium, menthol, peppermint oil, spearmint oil, herbmint oil), and a colorant may optionally be added. Preferably, the denture detergent of the invention contains 3–20% by weight, preferably 5–15% by weight, of polyethylene glycol as a humectant, 0.5–3% by weight, preferably 0.8–2.0% by weight, of hydrogenated castor oil as a solubilizing agent, 0.5–3% by weight, preferably 0.5–1.5% by weight, of peppermint oil as a flavor, 0.01–0.05% by weight, preferably 0.01–0.03% by weight, of food dye as a colorant.

EXAMPLES

The present invention is described in detail with reference to the following experiments and examples, and also, the effect of the invention is demonstrated.

Example 1

Tests of the Microbicidal Effect by the Microbicide for Detergents of the Invention Various inorganic carriers conjugated by silver ion as shown in Table 1 (commercial products), which can be used as a microbicide for detergents of the invention, were used in the test for evaluation of their microbicidal effect.

TABLE 1

| Trade Name | Manufacturer | Kind of the carrier |
| --- | --- | --- |
| Apacider AK | Sangi Co., Ltd. | hydroxyapatite |
| Silverace A-903K | Taihei Chemical Industrial Co., Ltd. | calcium phosphate |
| Rasap AN-600SA | Rasa Industries, Ltd. | aluminum phosphate |
| Novaron AGZ330 | Toagosei Co., Ltd. | zirconia phosphate |
| Zeomic AW10D | Shinanen Co., Ltd. | zeolite |
| Amenitop Ver-III | Matsushita Electric Industrial Co., Ltd. | silica gel |

Microorganism
 a) *Candida albicans* A (Candida)
 b) *Streptococcus pneumoniae* ATCC 49619 (*Streptcoccus pneumoniae*)
 c) *Staphylococcus aureus* IFO 3060 (*Staphylococcus aureus*)

Test Method

A microorganism-containing solution ($10^7$ CFU/mL) (1 mL) was added to an aqueous solution of a microbicide (0.01 w/v %) (100 mL), and the mixture was then incubated by stirring with a stirrer (200 rpm) at ambient temperature. Number of the microorganism in the solution was determined by a plate dilution test (fiber antimicrobial activity test) at each time.

Result

Figure 2:
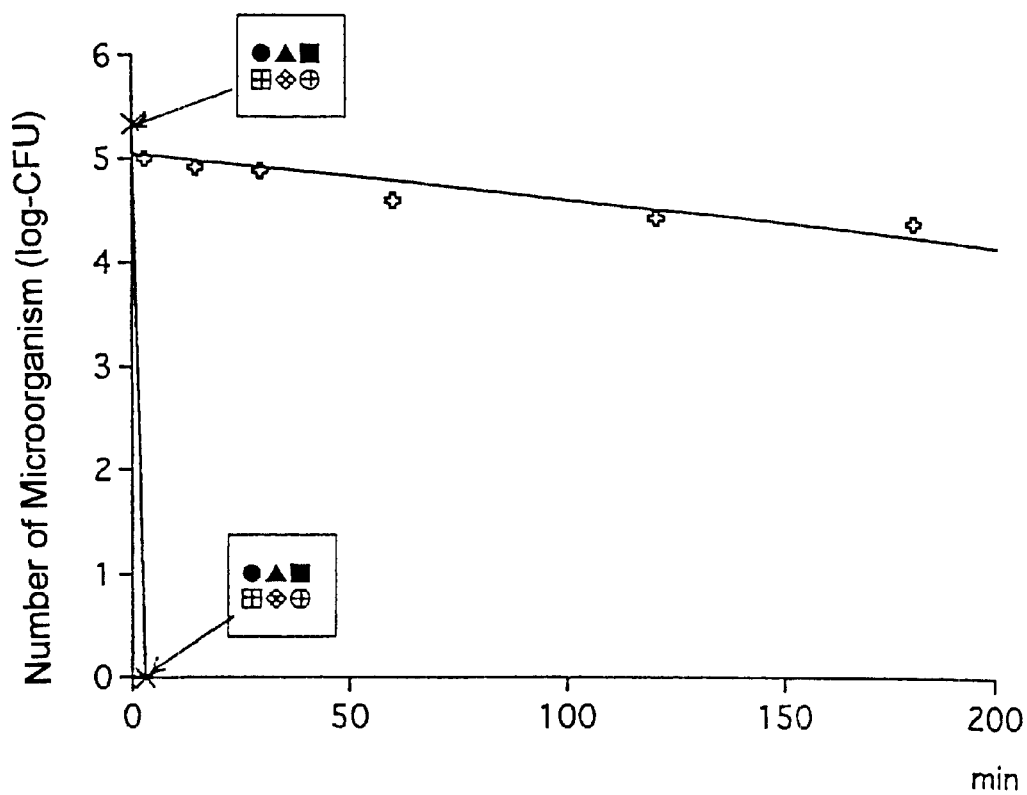
FIG. 2 is a graph showing the microbicidal effect of each microbicide on *Streptcoccus pneumoniae.*
Figure 3:
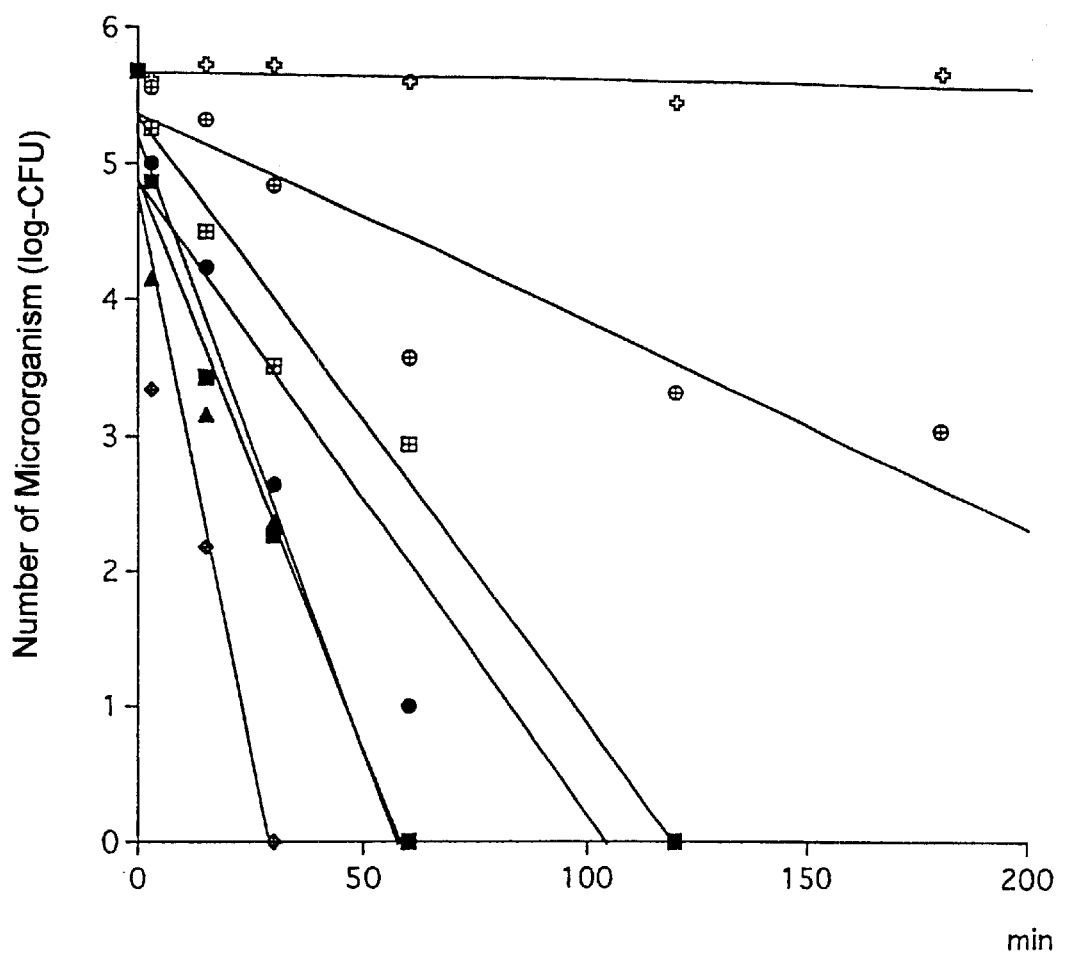
FIG. 3 is a graph showing the microbicidal effect of each microbicide on *Staphylococcus aureus.*

Change of the number of the microorganism with time is shown in FIG. 1 (Candida), FIG. 2 (*Streptcoccus pneumoniae*) and FIG. 3 (*Staphylococcus aureus*). The microbicidal activity is shown by D value (the time (minute) when the number of the microorganism is decreased to $\frac{1}{10}$), which was calculated by the following equation. Obtained values are shown in Table 2.

$$D = 1/k$$

k: a constant of death rate $= 1/t \log_{10} N_0/N_t$
t: treating time (minutes)
$N_0$: initial number of the microorganism
$N_t$: number of the survival microorganism after t minutes

TABLE 2

| D value of various inorganic microbicides | | | |
| --- | --- | --- | --- |
| | Candida | Streptcoccus pneumoniae | Staphylococcus aureus |
| Apacider AK | 65.6 | 0.6≧ | 21.3 |
| Silverace A-903K | 176.7 | 0.6≧ | 11.9 |
| Rasap AN-600SA | 37.0 | 0.6≧ | 11.1 |
| Novaron AGZ330 | 176.7 | 0.6≧ | 22.2 |
| Zeomic AW10D | 23.9 | 0.6≧ | 6.1 |
| Amenitop Ver-III | 1010.0 | 0.6≧ | 66.7 |

Zeomic (zeolite), Rasap (aluminum phosphate) and Apacider (hydroxyapatite) exhibited superior microbicidal effects on Candida and *Staphylococcus aureus*. Silverace (calcium phosphate) exhibited a superior antimicrobial effect on *Staphylococcus aureus*. All these microbicides exhibited excellent microbicidal effects on *Streptcoccus pneumoiae*.

Example 2

Formulation

A denture detergent containing 0.50% by weight of Apacider AK as a microbicide is prepared using the following ingredients:

TABLE 3

| Ingredient | % by weight |
|---|---|
| coated citric acid B | 30.00 |
| coated sodium percarbonate (PC-NS) | 31.00 |
| OXONE ($2KHSO_5 \cdot KHSO_4 \cdot K_2SO_4$) | 8.00 |
| sodium lauryl sulfate | 5.00 |
| sodium hydrogen carbonate | 10.60 |
| hydrogenated castor oil | 1.00 |
| food dye | 0.02 |
| peppermint oil | 0.88 |
| polyethylene glycol | 10.00 |
| synthetic aluminum silicate | 1.00 |
| magnesium oxide | 2.00 |
| Apacider AK | 0.50 |
| Total | 100.00 |

The above ingredients are mixed and compressed to form a tablet.

Example 3

Test for the Microbicidal Effect by the Denture Detergent

The denture detergent (3 g) of the invention prepared in Example 2 and the denture detergents A, B and C manufactured by other companies were each dissolved in 200 mL of water (so as to 1.5% aqueous solution), of which the microbicidal effects were tested.

Test Samples (1) Denture detergent of the invention. (as prepared in Example 2)

(2) Denture detergent A (3) Denture detergent B (4) Denture detergent C

Note) these denture detergents A, B and C manufactured by other companies have the microbicidal effects by active oxygen.

Microorganism a) *Candida albicans* A (Candida)

b) *Streptcoccus pneumoniae* ATCC 49619 (*Streptcoccus pneumoniae*)

c) *Staphylococcus aureus* IFO 3060 (*Staphylococcus aureus*)

Test Method

1. Preparation of a Microbe-applied Plate

The microorganism was inoculated in Trypto-soya broth, and subjected to stationary culture at 35° C. for 48 hours. The culture broth was centrifuged (9,000 rpm for 10 minutes) to collect the cells, and thereto was added a sterilized water (20 mL) to prepare a microbial suspension.

The microbial suspension was diluted so that its absorbance became in the range of $0.0750 \geq Abs \geq 0.0350$ to prepare a dipping solution. A standard curve was previously prepared, on which the range corresponding to $10^5$ CFU/mL was predetermined.

Toughron DE (Miki Chemical Product Co., Ltd.) was heated to polymerize, which was then cut in a size of 1.5×2.0 cm (0.2 cm in thickness) to prepare a resin plate. This plate was sterilized, followed by dipping in the dipping solution as prepared above at 25° C. for 3 hours to obtain a microbe-applied plate.

2. Evaluation of Microbicidal Effect

One tablet of the above denture detergent was each placed on the bottom of a 200 mL-graduated cylinder. A microbe-applied plate as prepared above was hanged in each cylinder, and tap water (200 mL) was immediately added thereto. The plate was taken out at each time predetermined. The plate was washed once with 20 mL of sterilized water, which was then incubated in a test tube containing Trypto-soya broth (15 mL) at 35° C. for 72 hours. The presence of microorganism was determined by checking the culture broth. It was determined by microscopically observing a turbid culture broth and identifying the microorganism using a selective medium.

Result

The time when the microorganism was no more detected in the culture broth, i.e., complete death time, was determined, and result for each microorganism is shown in Table 4. The longest time among those obtained from three independent experiments for each microorganism is shown in the table as the complete death time.

TABLE 4

| | Candida | Streptcoccus pneumoniae | Staphylococcus aureus |
|---|---|---|---|
| Denture detergent of the invention | 15 | 5 | 20 |
| Denture detergent A | 20 | 5 | 25 |
| Denture detergent B | 25 | 5 | 45 |
| Denture detergent C | 25 | 5 | 40 |

The denture detergent of the invention and the denture detergents A, B and C manufactured by other companies all exhibited superior microbicidal effects on *Streptococcus pneumoniae*, and their complete death times were within 5 minutes. For Candida and *Staphylococcus aureus*, the complete death time thereof by the denture detergent of the invention was both within 20 minutes, and the denture detergent of the invention thus exhibited superior microbicidal effect.

These results showed that the denture detergent of the invention has microbicidal effects greater than those of the denture detergents manufactured by other companies.

What is claimed is:

1. A denture detergent comprising 10–40% by weight of citric acid, 15–45% by weight of sodium percarbonate, 5–20% by weight of potassium hydrogen monopersulfate, 5–25% by weight of sodium hydrogen carbonate, 0.01–0.05% by weight of food dye, 1–15% by weight of sodium lauryl sulfate, 0.5–3% by weight of hydrogenated castor oil, 3–20% by weight of polyethylene glycol, 0.5–3% by weight of peppermint oil, 0.1–3% by weight of synthetic aluminum silicate, 1–5% by weight of magnesium oxide and 0.05–10% by weight of an inorganic carrier conjugated with an antimicrobial metal ion.

2. The denture detergent of claim 1 which is an effervescent tablet.

3. The denture detergent of claim 1, wherein the antimicrobial metal ion is silver, copper and/or zinc ion.

4. The denture detergent of claim 1, wherein the antimicrobial metal ion is silver ion.

5. The denture detergent of claim 1, wherein the inorganic carrier is a phosphate, a silicate or a carbonate.

6. The denture detergent of claim 5, wherein the phosphate is hydroxyapatite or tricalcium phosphate.

7. The denture detergent of claim 5, wherein the phosphate is hydroxyapatite.

8. The denture detergent of claim 1, wherein the inorganic carrier conjugated with an antimicrobial metal ion is in an amount of 0.1–3% by weight.

9. The denture detergent of claim 1, wherein the inorganic carrier conjugated with an antimicrobial metal ion is in an amount of 0.1–0.5% by weight.

* * * * *